United States Patent
Sulur et al.

(10) Patent No.: US 8,895,542 B2
(45) Date of Patent: Nov. 25, 2014

(54) MEDICINAL FUSIDIC ACID CREAM MADE USING SODIUM FUSIDATE AND INCORPORATING A BIOPOLYMER AND A PROCESS TO MAKE IT

(76) Inventors: Vanangamudi Subramaniam Sulur, Chennai (IN); Madhavan Srinivasan, Chennai (IN); Neelakandan Narayanan Chulliel, Chennai (IN); Haridas Sankar, Mumbai (IN); Kuppusamy Senthilkumar, Chennai (IN)

( * ) Notice: Subject to any disclaimer, the term of this patent is extended or adjusted under 35 U.S.C. 154(b) by 109 days.

(21) Appl. No.: 13/263,846

(22) PCT Filed: Apr. 12, 2010

(86) PCT No.: PCT/IB2010/051552
§ 371 (c)(1),
(2), (4) Date: Oct. 11, 2011

(87) PCT Pub. No.: WO2010/119385
PCT Pub. Date: Oct. 21, 2010

(65) Prior Publication Data
US 2012/0040946 A1   Feb. 16, 2012

(30) Foreign Application Priority Data
Apr. 13, 2009 (IN) .......................... 960/MUM/2009

(51) Int. Cl.
*A61K 31/575* (2006.01)
*A61P 31/04* (2006.01)
*A61P 17/02* (2006.01)
*A61K 9/00* (2006.01)
*A61K 47/36* (2006.01)
*A61K 47/10* (2006.01)
*A61K 47/06* (2006.01)

(52) U.S. Cl.
CPC ............. *A61K 31/575* (2013.01); *A61K 9/0014* (2013.01); *A61K 47/36* (2013.01); *A61K 47/10* (2013.01); *A61K 47/06* (2013.01)
USPC ..................... 514/182; 424/78.02; 424/78.06; 424/78.07

(58) Field of Classification Search
USPC .................. 424/78.02, 78.06, 78.07; 514/182
See application file for complete search history.

(56) References Cited

U.S. PATENT DOCUMENTS

| | | | | |
|---|---|---|---|---|
| 5,854,246 | A | * | 12/1998 | Francois et al. .......... 514/254.07 |
| 6,399,082 | B1 | * | 6/2002 | Ganemo ....................... 424/401 |
| 2007/0265352 | A1 | * | 11/2007 | Roeding et al. ............... 514/738 |
| 2007/0280971 | A1 | * | 12/2007 | Christensen et al. ......... 424/400 |
| 2008/0182819 | A1 | * | 7/2008 | Fuchino .......................... 514/55 |
| 2008/0194532 | A1 | | 8/2008 | Rabinovich-Guilatt et al. |
| 2008/0206161 | A1 | | 8/2008 | Tamarkin et al. |

FOREIGN PATENT DOCUMENTS

| | | |
|---|---|---|
| ES | 2204331 | 4/2004 |
| WO | 8603966 | 7/1986 |
| WO | WO 86/03966 | 7/1986 |
| WO | 2010070589 | 6/2010 |
| WO | WO 2010/070589 | 6/2010 |

OTHER PUBLICATIONS

Larsen et al. Acta Derm Venereol, 2007, 87, 62-68.*
Kumar, Reactive & Functional Polymers, 2000, 46, 1-27.*
Leo Laboratories Limited, Fucibet® Lipid Cream, revised on Mar. 29, 2012.*
Poyner et al. Comparative Efficacy and Tolerability of Fusidic Acid/Hydrocortisone Cream (Fucidin H cream) and Miconazole/Hydrocorticsone Cream (Daktacort Cream) in Infected Eczema, J Eur Acad Derm Ven, 1996, 7 (supplement 1), S23-S30; Abstract only.*
Page from "Pharmaceutics: The Science of Dosage Form Design," Aulton et al. eds., 2001.
English Abstract for ES2204331, published: Apr. 16, 2004; obtained: Dec. 9, 2013.

* cited by examiner

*Primary Examiner* — Gina Justice
*Assistant Examiner* — Genevieve S Alley

(57) ABSTRACT

Disclosed is a medicinal cream that includes flisidic acid which is made in situ under an oxygen-free environment using sodium fusidate. The fusidic acid is made by dissolving the sodium fusidate in a co-solvent under inert gas purging and under vacuum, and converting the sodium fusidate to fusidic acid in situ by adding an acid under stirring, The disclosed medicinal cream also includes a biopolymer and a cream base comprising at least one of each of a primary and secondary emulsifier, a waxy material, and water.

16 Claims, 1 Drawing Sheet

MEDICINAL FUSIDIC ACID CREAM MADE USING SODIUM FUSIDATE AND INCORPORATING A BIOPOLYMER AND A PROCESS TO MAKE IT

FIELD OF INVENTION

The present invention relates to primary and secondary bacterial skin infections and wounds including burn wounds. In particular it relates to a cream incorporating fusidic acid and a biopolymer in the form of chitosan and the process of making it and using it in treating these infections and wounds. Furthermore the Fusidic acid in the said cream has been created in situ using Sodium Fusidate as the starting Active Pharmaceutical Ingredient (API).

BACKGROUND OF INVENTION

Numerous treatments, both topical and systemic, are available for the primary and secondary skin infection caused by sensitive Gram +ve organisms such as *Staphylococcus aureus, Streptococcus* spp etc. Topical and systemic bacterial infection treatment compositions typically employ at least one active pharmaceutical ingredient (API) in combination with a base component. In the cream form, the APIs typically comprise an antibiotic/antibacterial such as Fusidic acid and the like.

In the currently available Fusidic acid creams, Fusidic acid in fine powder form is used as source API. The small particle size enhances its dermal contact by providing a large specific surface area and penetration, and provides a smooth feel on application to skin. However, a serious shortcoming of the fine size of Fusidic acid particles is that it presents an enormous surface area for contact and reaction with molecular Oxygen during manufacture, handling, and processing of the cream. This has serious implications to its chemical stability and results in rapid reduction in potency of the API (Fusidic acid) in the final cream formulation. Degradation due to oxidation is a major cause of instability of currently available Fusidic acid creams. Table 1 show that the degradation in the API samples (Fusidic acid) exposed to oxygen ranged between 7.7% and 11% for conditions ranging from room temperature to 45° C. when analysed at three months of exposure period at the above conditions.

It is known that greater the exposure time of Fusidic acid as the raw API to Oxygen, greater the limitations on stabilising Fusidic acid in a formulation. However, there is no published data on the stability of Fusidic acid over a period of time.

As an alternative to Fusidic acid, Sodium Fusidate is known to have been used to make dermaceutical medicaments for topical application. However, these are in the form of ointment rather than cream. Drawbacks of ointments over creams are well known and it's generally preferable to use creams rather than ointments for topical application.

Several aspects of Fusidic acid as an API are known:
  It is thermolabile
  It is available in cream formulations
  It can be obtained from Sodium Fusidate by dissolving the latter in an aqueous phase and adding acid to the solution, whereby Fusidic acid precipitates. However, the Fusidic acid precipitate is difficult to process into a cream form first due to its coarse and uneven particle size and second retrieving Fusidic acid from wet cake involves drying and further handling which deteriorates the Fusidic acid due to exposure to oxygen
The stability of the API in a Fusidic acid cream is unreliable due to the thermolabile nature of Fusidic acid Stabilization of medicaments containing Fusidic acid against oxidation involves observing a number of stringent precautionary procedures during manufacture and storage. These include:
  replacing Oxygen in pharmaceutical containers with inert gases such as Nitrogen, Carbon dioxide, Helium and the like
  avoiding contact of the medicament with heavy metal ions which catalyze oxidation,
  storing the API at reduced temperatures throughout its shelf life before processing
  In practice this means stricter controls during the manufacture as well as storage of such API (storing it typically at 2° C. to 8° C. in air-tight containers throughout their shelf life).

There is therefore a need to provide a process of making a Fusidic acid cream in which Fusidic acid will be of greater stability than the stability of the Fusidic acid in the conventional creams, particularly at the time of the manufacture of the cream, and which will sustain its stability at an acceptable level throughout its shelf life.

Next, let us look at the types of skin disorders and the methods of treatment available for them. Skin disorders can be broadly categorized as those arising from bacterial forms or fungi. Antifungal or antibacterial compositions are traditionally applied as lotions, creams or ointments. Furthermore in many instances, it is difficult to ascertain whether the skin condition is due to a bacterial agent or a fungus.

One approach to treating skin disorders is through elimination by trial and error. Antibacterial or antifungal compositions are applied in turn and response monitored and treatment modified. A major disadvantage of this approach is that treatment needs to be applied many times a day during the treatment period. This is greatly inconvenient and also not cost effective for a majority of human population, particularly in the under-developed nations.

There are several treatments available to treat skin disorders caused by bacteria or fungi. Typically, such compositions use steroids, antibacterial agents or antifungal agents, (or a fixed dose combination of these) and focus on these pharmaceutically active ingredients. The composition of such formulations is such as to enhance their physical/chemical/bio-release profile.

Many skin disorders caused by inflammation and bacterial attacks lead to itching and subsequent scratching, which, among other causes, can in turn lead to serious and complicated secondary infections. The conventionally available treatments do not focus on skin healing or rejuvenation; normally these two aspects are left to heal naturally.

The word healing as related to compromised skin conditions (cuts, wounds, infections, inflammations, abrasions, etc.) are not only about prevention, control, elimination of the source cause such as bacteria or fungi but also to restore the skin to its pre-infection state.

The current approaches of skin treatment can be broadly categorized into two stages, a. healing b. restoration of skin to pre-ailment state. The healing part comprises elimination, to the best possible extent, of the root cause of the disorder. This may be elimination of bacteria or fungi causing the infection through a suitable treatment of antibacterial or antifungal agents or reducing the inflammation through steroid treatment. While this treatment is under way, the ongoing compromised condition of the skin continues to be susceptible to secondary infections which can be of quite serious nature. In the case of scratched or wounded skin, it is important for blood clotting to occur quickly as it reduces chances of secondary infections. The focus of such treatments, which are administered through creams, lotions, ointments is on the action of active pharmaceutical ingredients. Cream bases or ointment bases are merely viewed as carriers to take APIs to the sites of disorder.

However, the aspect of restoring the skin back to its pre-disorder state is almost completely left to nature. Therefore one key drawback of the existing skin treatment approaches is that they run the risk of secondary infections due to slow blood clotting and wound healing process.

Furthermore, from the study of the prior art several lacking aspects of the existing prescription derma products used for topical treatment of skin disorders. This is manifested by the fact that the cream base matrix or the ointment base has been overlooked for any potential therapeutic benefits. In particular none of the available prior art suggests that:

Topical skin formulations can deliver skin healing or regeneration beyond the activity of the main APIs such that the therapeutic outcome of the main APIs is enhanced.

The addition of biologically active polymers (the so-called biopolymers) is a complex process in which the stability of the formulations could be compromised if the right biopolymer or naturally interacting formulation excipients or process parameters are not well thought through and optimized to enhance and complement therapy outcomes at the drug design stage itself.

Incorporation of a functionally bio-active excipient polymer in cream matrix while retaining the functional stability of the API in a single dose format of dermaceutical cream involves resolution of problems specific to the physical stability of cream matrix.

A look at some of the existing patents illustrates the above points. Fusidic acid has been used in cream form. The PCT application WO 2009063493 discloses a combination therapy of a topical antibiotic and a topical steroid for the treatment of inflammatory dermatoses associated with secondary bacterial infections. In particular it relates to topical pharmaceutical compositions comprising a combination of fusidic acid and corticosteroid such as Mometasone furoate useful in treatment of infected eczema's such as secondarily infected dermatitis, including secondarily infected contact dermatitis, psoriasis, allergic contact dermatitis and atopic dermatitis with secondary bacterial infections of skin. In particular it claims to relate to topical pharmaceutical compositions comprising a combination of fusidic acid and corticosteroid such as Mometasone furoate useful in prevention of infection in cases of dermatitis, especially atopic dermatitis sufferers who are at risk of getting secondary bacterial infection.

The application claims to derive inventiveness on the assertion that the then existing prior art failed to disclose the composition comprising a combination of fusidic acid with corticosteroids especially Mometasone or Halobetasol. The inventors of WO 2009063493 apparently surprisingly found that antibiotic action of fusidic acid and the anti-inflammatory effect of corticosteroid, such as Mometasone both play important roles in reducing S. aureus and improving patient's symptoms and signs of skin inflammatory infections. The inventors of WO 2009063493 also apparently surprisingly found that antibiotic action of fusidic acid and the anti-inflammatory effect of a corticosteroid such as Halobetasol, both play important roles in prevention of secondary bacterial infections in patients with non-infected dermatoses and in treatment of infected steroid responsive dermatoses such as secondarily infected dermatoses including secondarily infected contact dermatitis, allergic contact dermatitis, atopic dermatitis, psoriasis and other corticosteroid responsive dermatoses (CRD) with secondary bacterial infections of skin.

The invention disclosed in WO 2009063493 relates to a combination therapy of a topical antibiotic and a topical steroid for the treatment of inflammatory dermatoses associated with secondary bacterial infections. In particular the present invention relates to topical pharmaceutical compositions comprising a combination of fusidic acid and corticosteroid such as Mometasone furoate useful in treatment of infected eczema's such as secondarily infected dermatitis, including secondarily infected contact dermatitis, psoriasis, allergic contact dermatitis and atopic dermatitis with secondary bacterial infections of skin. In particular the present invention also relates to topical pharmaceutical compositions comprising a combination of fusidic acid and corticosteroid such as Mometasone furoate useful in prevention of infection in cases of dermatitis, especially atopic dermatitis sufferers who are at risk of getting secondary bacterial infection It is evident from the above example and other similar sources that the existing prior art does not teach or suggest:

Use of the cream base matrix as a functional element of the cream rather than a mere carrier for the main APIs Use a known bio-polymer as a functional excipient along with anti bacterial agent Sodium Fusidate Providing far superior healing effects as micro-film forming, blood clotting, supporting epidermal growth, microbial electrostatic immobilization take effect simultaneously rather than one after the other as would be the case in conventional single-drug therapy Improve overall medicinal properties of the cream, complimenting the API used in the cream matrix There is therefore a need for a single-dose API topical treatment that will be provided in a cream base, which cream base provides therapeutical value complementary to that provided by the main APIs and serves the purpose over and above that of being a mere carrier or delivery mechanism.

OBJECTS AND ADVANTAGES OF INVENTION

It is therefore one object of the present invention to provide a process of making a medicinal cream which contains Fusidic acid as the active API but which has greater stability of the API than the Fusidic acid manufactured using other means, throughout its shelf life, using a function cream base that contains chitosan that will provide an effective treatment against bacterial infections and also help actively heal the skin rejuvenate.

Another object of the present invention is to provide a medicinal cream that is effective in treatment of wounds including burn wounds.

Further objects of the present invention are to provide prescription medicinal formulations for topical skin treatment that:

Can deliver skin healing or regeneration beyond the activity of Sodium Fusidate such that the therapeutic outcome of the main API is enhanced.

Contain biologically active polymers (the so-called biopolymers) without compromising the stability of the formulations could be compromised if the right biopolymer is not selected.

Incorporate a functionally bio-active excipient polymer in cream matrix while retaining the functional stability of the API in a single dose format

SUMMARY OF INVENTION

Figure 1:
FIG. 1—Non-homogeneous nature of creams containing chitosan with non-compatible excipient such as carbomer FIG. 2—Film formation using chitosan

The present invention is directed to a medicinal composition for treating bacterial skin infections and related wounds, and also other skin wounds including those caused by burns. The cream also causes skin rejuvenation through an epithelisation process. The cream comprises:

a) a biopolymer in the form of Chitosan
b) an Active Pharmaceutical Ingredient (API), in the form of fusidic acid that has been generated in situ from sodium fusidate,
c) a cream base containing primary and secondary emulsifiers, waxy materials, co-solvents, acids, preservatives, buffering agents, anti oxidants, chelating agents, and humectants.
d) water.

The active ingredients, namely chitosan, and fusidic acid, are incorporated in cream base for use in treating bacterial skin infections with allergy & itching, & wounds on human skin involving contacting human skin with the above identified composition.

The invention also discloses a process to make the medicinal cream containing Fusidic acid which is formed in situ from Sodium Fusidate as the starting raw material, wherein Sodium Fusidate is converted into Fusidic acid under oxygen-free environment created using inert gas, preferably nitrogen, and chitosan. The cream produced by the process of the present invention has greater shelf-life stability and the finer particle size of the API than the conventional creams containing Fusidic acid. The cream produced by the process of the present invention contains Fusidic acid as the API that has been formed in situ from Sodium Fusidate, in a cream base comprising a preservative, an acid, a co-solvent, an emulsifier and a waxy material along with water, preferably purified water. The cream produced by the process of the present invention further optionally contains an ingredient selected from a group comprising, a buffering agent, an anti oxidant, a chelating agent, and a humectant, or any combination thereof.

DETAILED DESCRIPTION OF INVENTION

We discussed earlier the known aspects of the topical preparations that have Fusidic acid and Sodium Fusidate as the APIs. It is evident from the current state of knowledge that:

Creams containing Fusidic acid that is made using Sodium Fusidate as starting API are not available.
There is no published data on the stability of Sodium Fusidate as the API.
Sodium Fusidate is not considered to be inherently more stable as an API than Fusidic acid.
Creams containing chitosan and fusidic acid which has been created in situ from sodium fusidate is not commercially available.

In the face of this, it has been surprisingly discovered that Sodium Fusidate as an API is significantly more stable than Fusidic acid and that Fusidic acid deteriorates more rapidly than Sodium Fusidate.

There is no published data on the stability of Sodium Fusidate as the API. The applicant carried out experiments on Sodium Fusidate to evaluate its stability. It can be seen from Table 2 that the degradation of Sodium Fusidate over a temperature range of room temperature to 45° C. ranged between 2.45% and 6%.

Tables 1 and 2 also show the comparison between the stability of the Fusidic acid and Sodium Fusidate as raw APIs. The study was carried out using an in-house HPLC method developed by the applicant, which the applicant believes is a true stability-indicating method as opposed to the titration method suggested in British Pharmacopoeia (BP). This is because the BP method does not differentiate between the intact API and the degraded form.

Stability Analysis of Fusidic Acid

TABLE 1

Results Of 3-Month-Old Fusidic Acid (API) Analysis By Stability Indicating HPLC Method And Titration Method

| S. No | Conditions | *Initial (%) | Fusidic Acid Assay (%) Titration | HPLC | Percentage Drop (%) Titration | HPLC | Remarks |
|---|---|---|---|---|---|---|---|
| 1 | RT (Open) | 100.6 | 99.21 | 92.93 | 1.39 | 7.67 | API |
| 2 | RT (Closed) | | 99.02 | 94.37 | 1.58 | 6.23 | analysed |
| 3 | 45° C. (Open) | | 98.52 | 89.52 | 2.08 | 11.08 | After 3 |
| 4 | 45° C. (Closed) | | 99.10 | 92.12 | 1.50 | 8.48 | Months |

Name of the Sample: FUSIDIC ACID BP
Pack: Open & Closed Petri dish

Stability Analysis of Sodium Fusidate

TABLE 2

Results Of 3 Months Old Sodium Fusidate (API) Analysis By Stability Indicating HPLC Method And Titration Method

| S. No | Conditions | *Initial (%) | Sodium Fusidate Assay(%) Titration | HPLC | Percentage (%) Titration | HPLC | Remarks |
|---|---|---|---|---|---|---|---|
| 1 | RT (Open) | 98.7 | 97.71 | 96.25 | 0.99 | 2.45 | API |
| 2 | RT (Closed) | | 98.85 | 97.67 | −0.15 | 1.03 | analysed |
| 3 | 45° C. (Open) | | 97.07 | 92.65 | 1.63 | 6.05 | After 3 |
| 4 | 45° C. (Closed) | | 97.16 | 92.96 | 1.54 | 5.74 | Months |

Name of the Sample: Sodium Fusidate BP
Pack: Open & Closed Petri dish
In both studies the * Initial denotes the results of the samples tested at the time of receipt of the API from the supplier.

It can be observed from Tables 1 and 2 that:
In the case of Fusidic Acid, there is about 7.7% loss in 3 Months at room temperature (open condition) and about 11% loss in 3 Months at 45° C. (open condition).
In the case of Sodium Fusidate, there is about 2.5% loss in 3 Months at room temperature (open condition) and about 6% loss in 3 Months at 45° C. (open condition).

The data thus shows that Sodium Fusidate as an API is more stable than Fusidic acid.

The applicants explored the possibility of making a cream (rather than an ointment) containing chitosan and Sodium Fusidate (rather than Fusidic acid) as the starting raw material. Although Sodium Fusidate has been used in dermaceutical applications, it has not been possible to make creams that use Sodium Fusidate. This is because of the inherent alkalinity of Sodium Fusidate (pH 7.5 to 9), which means it cannot be used in a cream form therefore all products manufactured using Sodium Fusidate as starting material are ointments. A dermaceutical cream that uses Sodium Fusidate would exploit the benefit of the fact that Sodium Fusidate is more stable than Fusidic acid and it would also provide a cream formulation which is far superior in its application qualities than an ointment. It would thus fill an existing need for a cream that has better stability than currently available creams containing Fusidic acid.

The applicant therefore surprisingly discovered that in order to achieve greater stability of the API in a dermaceutical cream, Sodium Fusidate rather than Fusidic acid may be used as the starting API during the cream's manufacture. Using Sodium Fusidate as starting material eliminates the drawback associated with the manufacture and storage of existing Fusidic acid creams.

The applicant has also discovered that the Fusidic acid cream prepared using Sodium Fusidate as the starting API shows good chemical stability, efficacy, and microbial sensitivity.

The application discloses a process of making a cream containing Fusidic acid (the API) that has been prepared using Sodium Fusidate as the starting API, in which Fusidic acid forms in-situ under totally oxygen-free environment created using inert gas, preferably nitrogen, by slow addition of an acid, into a molecular dispersion form (due to the presence of a co-solvent) at the intermediate stage, and which Fusidic acid regenerates as an extremely fine dispersion when added to a final cream base, thereby resulting in a finely and homogeneously dispersed Fusidic acid in the final cream. All these operations are performed in an environment free of atmospheric oxygen created using inert gas, preferably nitrogen. The cream made using the process of the present invention contains Fusidic acid as the API that has been formed in situ from Sodium Fusidate, in a cream base comprising a buffering agent, a preservative, an acid, a co-solvent, an emulsifier and a waxy material along with water, preferably purified water.

The Sodium Fusidate which may be employed in the process of the present invention as starting API is well known in the art of treating bacterial primary and secondary infections.

The active compound Sodium Fusidate require a base component to be used in the pharmaceutical composition that uses the compound, since the compound cannot, by themselves, be deposited directly on to human skin due to their harshness.

The base component usually contains a biopolymer, primary and secondary emulsifiers, waxy materials, co-solvents, acids, preservatives, purified water and the like.

The cream base of the cream made using the process of the present invention optionally further comprises an ingredient selected from a group comprising an anti oxidant, a chelating agent, and a humectant, or any combination thereof.

The present invention provides a process to make a novel cream that has been produced using Sodium Fusidate as the starting raw material, and which cream contains Fusidic acid of high therapeutic efficacy and of chemical stability that is generally superior to the commercially available creams containing Fusidic acid.

The Fusidic acid cream made using the process of the present invention has been manufactured in a totally oxygen free environment under purging with inert gas and applying vacuum, the inert gas being preferably nitrogen. Under these conditions, the Sodium Fusidate is converted in situ into Fusidic acid. The cream of the present invention is used in the treatment of bacterial skin infections.

From the study of the prior art several lacking aspects of the existing topical treatment formulations in the field of prescription medications are evident. The prior art does not teach or suggest that:

Topical skin formulations can deliver skin healing or regeneration beyond the activity of the main APIs such that the therapeutic outcomes of the main APIs are enhanced.

The addition of biologically active polymers (the so-called biopolymers) is a complex process in which the stability of the formulations could be compromised if the right biopolymer is not selected.

Incorporation of a functionally bio-active excipient polymer in cream matrix while retaining the functional stability of the API in a single dose format of dermaceutical cream involves resolution of problems specific to the physical stability of cream matrix.

Examples of suitable topical antibacterial agents, which may be used, include, but are not limited to Neomycin Sulphate, Sodium Fusidate, Calcium Mupirocin, Gentamycin, Silver Sulphadiazine, Ciprofloxacin, Framycetin Sulphate, Quinidochlor, Povidone-Iodine, Sisomicin, Nitrofural and the like.

Examples of suitable biopolymer, which may be used, include, but are not limited to chitosan and the like.

Chitosan

Chitosan is a linear polysaccharide composed of randomly distributed $\beta$-(1-4)-linked D-glucosamine (deacetylated unit) and N-acetyl-D-glucosamine (acetylated unit). It is known to have a number of commercial uses in agriculture and horticulture, water treatment, chemical industry, pharmaceuticals and biomedics.

It's known properties include accelerated blood clotting. However, it is not known to a person skilled in the art that chitosan's behaviour with a pharmaceutical active ingredient such as an antibacterial or antifungal agent needs to be treated with caution.

It is known to have film forming, mucoadhesive and viscosity-increasing properties and it has been used as a binder and disintegrating agent in tablet formulations.

Chitosan generally absorbs moisture from the atmosphere/environment and the amount absorbed depends upon the initial moisture content, temperature and relative humidity of the environment.

It is regarded as a non-toxic and non-irritant material. It is biocompatible with both healthy and infected skin and has been shown to be biodegradable as it is derived from shrimps, squids and crabs.

Chitosan due to its unique physical property accelerates wound healing and wound repair. It is positively charged and soluble in acidic to neutral solution. Chitosan is bioadhesive and readily binds to negatively charged surfaces such as mucosal membranes. Chitosan enhances the transport of polar drugs across epithelial surfaces. Chitosan's properties allow it to rapidly clot blood, and it has recently gained approval in the USA for use in bandages and other hemostatic agents.

Chitosan is nonallergenic, and has natural anti-bacterial properties, further supporting its use. As a micro-film forming biomaterial, chitosan helps in reducing the width of the wound, controls the oxygen permeability at the site, absorbs wound discharge and gets degraded by tissue enzymes which are very much required for healing at a faster rate. It also reduces the itching by providing a soothing effect. It also acts like a moisturizer. It is also useful in treatment of routine minor cuts and wounds, burns, keloids, diabetic ulcers and venous ulcers. Chitosan used in the present invention comes in various molecular weights ranging from 1 kdal to 5000 kdal.

Chitosan is discussed in the US Pharmacopoeia forum with regard to its functional excipient category. Since chitosan is basically a polymer, it is available in various grades depending upon the molecular weight. The various grades of chitosan include chitosan long chain, chitosan medium chain & chitosan short chain. The grades long, medium & short chain directly corresponds to the molecular weight of the chitosan.

Generally the long chain grade has a molecular weight in the range of 500,000-5,000,000 Da, the medium chain grade has a molecular weight in the range of 1,000,000-2,000,000 Da and the short chain grade has a molecular weight in the range of 50,000-1,000,000 Da.

The molecular weight of the chitosan plays an important role in the formulation. Higher molecular weight chitosan imparts a higher viscosity to the system and lower molecular weight chitosan imparts a lower viscosity to the system. However the medium chain grade chitosan delivered an optimum level of viscosity to the formulation. Since the dosage form is a cream, appropriate levels of viscosity is required to achieve a good spreadability over the skin.

The inventors finalized the chitosan medium chain grade for the present invention since it imparted the required rheologic properties to the cream without compromising the therapeutic activity of the actives, ie Sodium Fusidate as the starting active and chitosan. The concentration of chitosan medium chain grade was carefully arrived based on several in house trials and Preclinical animal studies for efficacy.

Topical Anti-Bacterials

Topical Anti-bacterials are intended to target skin for bacterial infections caused by *Staphylococcus aureus, Staphylococcus epidermidis, Methicillin Resistance Staphylococcus Aureus* (MRSA) etc.

Anti-bacterials act by inhibiting cell wall synthesis by combining with bacterial ribosomes and interfering with mRNA ribosome combination.

In another hypothesis it is believed that anti-bacterials induce ribosomes to manufacture peptide chains with wrong amino acids, which ultimately destroy the bacterial cell.

Sodium Fusidate

Sodium Fusidate belongs to the group of medicines known as antibiotics. It is used to treat bacterial infections, such as infections of the joints and bones by killing or stopping the growth of the bacteria responsible.

The molecular formula of Sodium Fusidate is $C31H47$. The chemical name is $3\mu,11\mu,16\beta$-Trihydroxy 29-nor-$8\mu, 9\beta, 13\mu, 14\beta$-dammara-17(20) [10,21-cis], 24-dien-21-oic acid 16-acetate, sodium salt. It is a white colour crystalline powder soluble in one part of water at 20° C.

Pharmacology & Mechanism of Action

Sodium Fusidate inhibits bacterial protein synthesis by interfering with amino acid transfer from aminoacyl-sRNA to protein on the ribosomes. Sodium Fusidate may be bacteriostatic or bactericidal depending on inoculum size.

Although bacterial cells stop dividing almost within 2 minutes after contact with the antibiotic in vitro, DNA and RNA synthesis continue for 45 minutes and 1 to 2 hours, respectively. Sodium Fusidate is virtually inactive against gram-negative bacteria. The differences in activity against gram-negative and gram-positive organisms are believed to be due to a difference in cell wall permeability.

Mammalian cells are much less susceptible to inhibition of protein synthesis by Sodium Fusidate than sensitive bacterial cells. These differences are believed to be due primarily to a difference in cell wall permeability.

Indications: Sodium Fusidate is indicated for the treatment of primary and secondary skin infections caused by sensitive strains of *S. aureus, Streptococcus* species and *C. minutissimum*. Primary skin infections that may be expected to respond to treatment with Sodium Fusidate topical include: impetigo contagiosa, erythrasma and secondary skin infections such as infected wounds and infected burns.

Most of the topical products are formulated as either creams or ointments. A cream is a topical preparation used for application on the skin. Creams are semi-solid emulsions which are mixtures of oil and water in which APIs (Active Pharmaceutical Ingredients) are incorporated. They are divided into two types: oil-in-water (O/W) creams which compose of small droplets of oil dispersed in a continuous water phase, and water-in-oil (W/O) creams which compose of small droplets of water dispersed in a continuous oily phase. Oil-in-water creams are user-friendly and hence cosmetically acceptable as they are less greasy and more easily washed with water. An ointment is a viscous semisolid preparation containing APIs, which are used topically on a variety of body surfaces. The vehicle of an ointment is known as ointment base. The choice of a base depends upon the clinical indication of the ointment, and the different types of ointment bases normally used are:

Hydrocarbon bases, e.g. hard paraffin, soft paraffin
Absorption bases, e.g. wool fat, bees wax Both above bases are oily and greasy in nature and this leads to the undesired effects like difficulty in applying & removal from the skin. In addition this also leads to staining of the clothes. Most of the topical products are available as cream formulation because of its cosmetic appeal.

The acidic scale of pH is from 1 to 7, and the base scale of pH is from 7 to 14. Human skins pH value is some where between 4.5 and 6. Newborn baby's skin pH is closer to neutral (pH 7), but it quickly turns acidic. Nature has designed this probably to protect young children's skin, since acidity kills bacteria. As people become older, the skin becomes more and more neutral, and won't kill as many bacteria as before. This is why the skin gets weak and starts having problems. The pH value goes beyond 6 when a person actually has a skin problem or skin disease. This shows that it is necessary to choose topicals that have a pH value close to that of skin of a young adult.

A slight shift towards the alkaline pH would provide a better environment for microorganisms to thrive. Most of the topical products are available as creams. Active compounds in cream formulations are available in ionized state, whereas in case of ointments these are present in non-ionized state. Generally, the cream formulations are the first choice of the formulators in design and development of topical dosage forms, as the cream formulations are cosmetically elegant, and also as the active compound is available in ionized state, and the drug can penetrate the skin layer fast which makes the formulation totally patient friendly.

The pH of the Chitosan Cream with antibacterial agent—Sodium Fusidate of the present invention is from about 3 to 6. On the other hand, ointments that are commercially available are greasy and cosmetically non elegant. Furthermore, as the active compound in an ointment is in non-ionized form, the penetration of skin is slow.

It is essential that the active drug penetrates the skin for the optimum bio-dermal efficacy. The particle size of the active drug plays an important role here. It is necessary that the active drug is available in colloidal or molecular dispersed state for the product being highly efficacious form. Also this is to be achieved in the safe pH compatible environment of skin (4.0 to 6.0). To achieve all these, it is essential to choose proper vehicles or co-solvents for the dissolution or dispersion of the drug. The product of the present invention is highly efficacious due to the pronounced antibacterial & wound healing activity of the active ingredients, which are available in ultra micro-size, colloidal form, which enhances skin penetration.

Rationale for Combining Fusidic Acid Made from Sodium Fusidate and Chitosan:

Numerous topical treatments are currently employed for the treatment of bacterial infections. However there is no effective single-dose therapy for protecting the skin, controlling superficial bleeding, wounds and burns. To meet this need and to bring affordable and safe therapy to the dispersed segment of population across all countries/communities, a therapy with unique combination of Chitosan, a biopolymer with skin rejuvenation properties with Sodium Fusidate is proposed as a novel cream.

Topical Sodium Fusidate have profound efficacy in primary & secondary bacterial skin infections of varied etiology due to its antibacterial properties. A drawback of the monotherapy with any topical antibacterial has been the relatively slow onset of the effect.

By employing Sodium Fusidate & chitosan in a formulation, the properties of both antibacterial and chitosan are optimized. As chitosan is film forming, biocompatible, non-allergenic material it helps in protecting the skin by acting as a barrier. It further controls the superficial bleeding caused by scratching and also arrests the mobility of pathogens due to its cationic charge.

The properties of Sodium Fusidate and chitosan's skin regenerative aspects are well exploited in the present invention and the maximum therapeutic benefit is passed on to the patient thereby aiding in faster healing. This ensures that the patient would benefit for the treatment of skin wounds, burns with bacterial infections.

The inclusion of chitosan in the formulation takes care of many attributes, which are considered to be very much essential in treating skin ailments. The combination of chitosan with Sodium Fusidate is unique and novel since this is not available commercially across the globe.

The concept of the combination is justified by considering the physical, chemical and therapeutic properties of chitosan used in combination with fusidic acid made in situ from Sodium Fusidate.

Other Inventive Aspects of the Present Invention:

Another inventive aspect of the present invention is that the addition of a functional excipient in the cream base is not a straight forward process of mere addition. The inventor has found that the compatibility of the functional excipient such as chitosan with other agents in the cream is of critical importance. This is because incompatibility would compromise the stability of the final product. As examples, the inventors have found that well known excipients such as Xanthan Gum and carbomer which have been variously used as stabilizing agents, cannot be used in combination with functional biopolymers such as chitosan.

Excipients for topical dosage forms include Polymers, Surfactants, Waxy Materials, and Emulsifiers etc. Polymers are used as gelling agents, suspending agents, viscosity builders, release modifiers, diluents, etc. Surfactants are used as wetting agents, emulsifiers, solubilising agents release enhancers, etc.

Generally polymers & surfactants may or may not possess ionic charge. They may be anionic or cationic or non-ionic in nature. If anionic excipients are included in the formulation they interact with cationic formulation excipients and produce products which are not homogenous, aesthetically not appealing and give rise to unwanted by products, possible allergens, impurities, toxic substances etc due to incompatibility.

Since the dosage is for the treatment of ailing patients, these incompatibilities in the products cannot be accepted and these add more complication to the patients.

The inventors carefully screened the excipients which included the polymers and surfactants for developing a formulation. A thorough study was performed after screening the short listed excipients. The possible interactions between the excipients were given much focus and detailed experiments were done.

To quote some examples about the anionic-cationic interaction in the cream dosage form the inventors made some formulations of Sodium Fusidate (see tables 3-7) containing Xanthan Gum & Chitosan, Acrylic acid polymer & Chitosan, Sodium Lauryl Sulphate & Chitosan, Docusate Sodium & Chitosan and Gum Arabic & Chitosan. The results clearly indicated the occurrence of interactions which was very much visible and seen as lumps into the entire system. The final product was also not aesthetically appealing without homogeneity. The attached FIG. 1 clearly explains the interaction between chitosan and unsuitable anionic excipients. Based on the observations and thorough knowledge about the excipients, the inventors arrived at a robust formula without any possible interactions.

TABLE 3

Fusidic Acid Cream incorporating Chitosan and Xanthan Gum

| S. No | Ingredients | % w/w |
|---|---|---|
| 1 | Sodium Fusidate (equivalent to make Fusidic acid 2%) | 2.08 |
| 2 | Chitosan | 0.25 |
| 3 | Lactic acid | 0.1 |
| 4 | Xanthan Gum | 1.0 |
| 5 | Cetostearyl Alcohol | 12.5 |
| 6 | White Soft Paraffin | 12.5 |
| 7 | Polysorbate 80 | 2 |
| 8 | Propylene Glycol | 25 |
| 9 | Benzoic Acid | 0.2 |
| 10 | Butylated Hydroxy Toluene | 0.01 |
| 11 | Disodium Edetate | 0.1 |
| 12 | 1M Nitric Acid solution | 4 |
| 13 | Disodium hydrogen ortho phosphate | 0.5 |
| 14 | Purified Water | 40 |

TABLE 4

Fusidic acid cream incorporating chitosan and acrylic acid polymer

| S. No | Ingredients | % w/w |
|---|---|---|
| 1 | Sodium Fusidate (equivalent to make Fusidic acid 2%) | 2.08 |
| 2 | Chitosan | 0.25 |
| 3 | Lactic acid | 0.1 |
| 4 | Acrylic Acid Polymer | 1.0 |
| 5 | Cetostearyl Alcohol | 12.5 |
| 6 | White Soft Paraffin | 12.5 |
| 7 | Polysorbate 80 | 2 |
| 8 | Propylene Glycol | 25 |
| 9 | Benzoic Acid | 0.2 |
| 10 | Butylated Hydroxy Toluene | 0.01 |
| 11 | Disodium Edetate | 0.1 |
| 12 | 1M Nitric Acid solution | 4 |
| 13 | Disodium hydrogen ortho phosphate | 0.5 |
| 14 | Purified Water | 40 |

TABLE 5

Fusidic acid cream incorporating chitosan & sodium lauryl sulphate

| S. No | Ingredients | % w/w |
|---|---|---|
| 1 | Sodium Fusidate (equivalent to make Fusidic acid 2%) | 2.08 |
| 2 | Chitosan | 0.25 |

TABLE 5-continued

Fusidic acid cream incorporating chitosan & sodium lauryl sulphate

| S. No | Ingredients | % w/w |
|---|---|---|
| 3 | Lactic acid | 0.1 |
| 4 | Sodium Lauryl Sulphate | 1.0 |
| 5 | Cetostearyl Alcohol | 12.5 |
| 6 | White Soft Paraffin | 12.5 |
| 7 | Polysorbate 80 | 2 |
| 8 | Propylene Glycol | 25 |
| 9 | Benzoic Acid | 0.2 |
| 10 | Butylated Hydroxy Toluene | 0.01 |
| 11 | Disodium Edetate | 0.1 |
| 12 | 1M Nitric Acid solution | 4 |
| 13 | Disodium hydrogen ortho phosphate | 0.5 |
| 14 | Purified Water | 40 |

TABLE 6

Fusidic acid cream incorporating chitosan and docusate sodium

| S. No | Ingredients | % w/w |
|---|---|---|
| 1 | Sodium Fusidate (equivalent to make Fusidic acid 2%) | 2.08 |
| 2 | Chitosan | 0.25 |
| 3 | Lactic acid | 0.1 |
| 4 | Docusate Sodium | 1.0 |
| 5 | Cetostearyl Alcohol | 12.5 |
| 6 | White Soft Paraffin | 12.5 |
| 7 | Polysorbate 80 | 2 |
| 8 | Propylene Glycol | 25 |
| 9 | Benzoic Acid | 0.2 |
| 10 | Butylated Hydroxy Toluene | 0.01 |
| 11 | Disodium Edetate | 0.1 |
| 12 | 1M Nitric Acid solution | 4 |
| 13 | Disodium hydrogen ortho phosphate | 0.5 |
| 14 | Purified Water | 40 |

TABLE 7

Fusidic acid cream incorporating chitosan and gum arabic

| S. No | Ingredients | % w/w |
|---|---|---|
| 1 | Sodium Fusidate (equivalent to make Fusidic acid 2%) | 2.08 |
| 2 | Chitosan | 0.25 |
| 3 | Lactic acid | 0.1 |
| 4 | Gum Arabic | 1.0 |
| 5 | Cetostearyl Alcohol | 12.5 |
| 6 | White Soft Paraffin | 12.5 |
| 7 | Polysorbate 80 | 2 |
| 8 | Propylene Glycol | 25 |
| 9 | Benzoic Acid | 0.2 |
| 10 | Butylated Hydroxy Toluene | 0.01 |
| 11 | Disodium Edetate | 0.1 |
| 12 | 1M Nitric Acid solution | 4 |
| 13 | Disodium hydrogen ortho phosphate | 0.5 |
| 14 | Purified Water | 40 |

The above products (tables 3 to 7) are examples of products that do not form homogeneous creams, but produce non-homogeneous creams of the type illustrated in FIG. 1. Yet the proportions stated in these examples are the ones that a person skilled in the art may use based currently available knowledge. Only after a thorough and extensive trials and errors would it be possible to arrive at right types and proportions of excipients.

As we have also discussed earlier, in a therapy, Fusidic acid provides relief against bacterial infections. However, the aspects such as like skin protection, bleeding at the site, mobility of pathogens from one site to another, etc are not addressed so far in a single dose therapy that includes fusidic acid generated in situ from sodium fusidate.

This present invention with its single-dose application fills this gap by incorporating chitosan and tapping the required benefits of skin protection (by way of film forming property), stopping the bleeding (by way of blood clotting property) and immobilization of pathogenic microbes (due to its cationic electrostatic property).

Therapeutic value addition by incorporation of a functional excipient in the form of a chitosan which is a biopolymer in the cream matrix is an integrated sub-set of the following functional attributes of the biopolymer:

formulation of a micro-film on the skin surface accelerated blood clotting as compared to creams that do not contain film-forming biopolymers electrostatic immobilisation of surface microbes due to cationic charge of the biopolymer significant enhancement of the skin epithelisation or regeneration which is of particular help in skin damage caused by severe infections as well as wounds and burns The inventive efforts involved in developing the platform technology covered by incorporation of a functional biopolymer in prescription dermaceutical products is:

in identification of the complementary therapeutic value that such incorporation delivers in identification of issues related to physio-chemical stability of the product resulting from the incorporation of the biopolymer in providing a single dose format where the bacterial infection has been identified The importance of a single dose treatment, particularly in the underdeveloped countries cannot be overemphasized. In absence of access to a general physician in most parts of south Asia or Africa, let alone a skin specialist, a single dose formulation dramatically increases chances of eliminating root cause of the skin disorder while also allowing the skin to regenerate.

During dermatological conditions, currently available therapies do not address the issues like protecting the skin, arresting the bleeding etc. The unique innovative formulation of the present invention takes care of the skin conditions by treating them along with controlling the superficial bleeding at the site. It is well understood that if the superficial bleeding is left untreated, it will lead to secondary microbial infections. The present invention advantageously provides a solution to this unmet need.

Further, with ever increasing pressures on medical support systems and the attendant scarcity/high cost of the same, there is an emergent need all across the globe to address the following issues in such cases—

Patients waiting too long for treatment

Staying unnecessarily long when they get to hospital

Having to come back more often than they need to

Reducing the length of stay is a key underlying problem to be tackled in most cases. The present invention with its single-dose therapy reduces the overall treatment time of a serious skin disorder significantly.

Details of the Medicinal Cream of the Present Invention and Processes of Manufacturing it:

These are provided in the form of various embodiments that describe the product of the present invention and the processes to make it.

Preferred Embodiment No. 1: A medicinal cream for topical treatment of bacterial skin infections, and for related wound healing, wherein said cream comprises an antibacterial agent, Sodium Fusidate, and a biopolymer provided in a cream base, said cream base comprising at least one of each of a preservative, a primary and a secondary emulsifier, a waxy material, a co-solvent, an acid, and water, preferably purified water.

Embodiment No. 1: A medicinal cream as disclosed in the preferred embodiment no 1, wherein said cream further comprising any of a group comprising a buffering agent, an antioxidant, a chelating agent, a humectant, or any combination thereof.

Embodiment No. 2: A novel dermaceutical cream as disclosed in the preferred embodiment no 1 and the embodiment no. 1, wherein
  said Fusidic acid is present in an amount from about 0.1% (w/w) to about 25% (w/w), preferably from about 0.5% (w/w) to about 5% (w/w), and more preferably about 2.00% (w/w), and in which the amount of said Sodium Fusidate used to form in situ said Fusidic acid is in the range between about 0.1% (w/w) to about 25% (w/w), preferably from about 0.5% (w/w) to about 5% (w/w) and more preferably about 2.08% (w/w), and
  said biopolymer is in the form of chitosan, added in an amount between about 0.01% and about 1% by weight, preferably from about 0.01% w/w to about 0.5% w/w and most preferably about 0.25% w/w,
  said primary and secondary emulsifiers are selected from a group comprising Cetostearyl alcohol, Cetomacrogol-1000, Polysorbate-80, Span-80 and the like and added in an amount from about 1% (w/w) to 20% (w/w); said waxy materials is selected from a group comprising white soft paraffin, liquid paraffin, hard paraffin and the like, or any combination thereof, and added in an amount from about 5% (w/w) to 30% (w/w); said co-solvent is selected from a group comprising Propylene Glycol, Hexylene Glycol, PolyEthylene Glycol-400, Isopropyl Myristate and the like, or any combination thereof, and added in an amount from about 5% (w/w) to 50% (w/w); said acid is selected from a group comprising HCl, $H_2SO_4$, $HNO_3$, Lactic acid and the like, or any combination thereof, and added in an amount from about 0.005% (w/w) to 0.5% (w/w); said preservative is selected from a group comprising Methylparaben, Propylparaben, Chlorocresol, Potassium sorbate, Benzoic acid and the like, or any combination thereof, and added in an amount from about 0.05% (w/w) to 0.5% (w/w); said water is added in the amount in the range of 20% (w/w) to 75% (w/w), preferably 30% (w/w) to 50% (w/w), more preferably 35% (w/w) to 45% (w/w), preferably purified water.

Embodiment No. 3: A novel medicinal cream as disclosed in the preferred embodiment no 1 and embodiment 2 further comprising a buffering agent which is selected from a group comprising Di Sodium Hydrogen Ortho Phosphate, Sodium Hydrogen Ortho Phosphate and the like, or any combination thereof, and added in an amount from about 0.001% (w/w) to 1.00% (w/w).

Embodiment No. 4: A novel medicinal cream as disclosed in the preferred embodiment no 1 and embodiments 2 and 3 further comprising an antioxidant which is selected from a group comprising Butylated Hydroxy Anisole, Butylated Hydroxy Toluene and the like, or any combination thereof, and added in an amount from about 0.001% (w/w) to 1% (w/w).

Embodiment No. 5: A novel medicinal cream as disclosed in the preferred embodiment no 1 and embodiments nos. 2 to 4 further comprising a chelating agent which is selected from a group comprising Disodium EDTA and the like, or any combination thereof, and added in an amount from about 0.05% (w/w) to 1% (w/w).

Embodiment No. 6: A novel medicinal cream as disclosed in the preferred embodiment no 1, and embodiments nos. 2 to 5 further comprising a humectant which is selected from a group comprising Glycerin, Sorbitol, Propylene Glycol and the like, or any combination thereof, and added in an amount from about 5% (w/w) to 50% (w/w).

Preferred Embodiment 2: The preferred embodiment of the invention discloses a process to make a dermaceutical cream containing Fusidic acid, said process comprising the step of using sodium fusidate as the raw API and converting it in situ into Fusidic acid under oxygen-free environment in a cream base.

Embodiment No. 7: In an embodiment of the present invention the process of making the composition is disclosed, wherein the step of converting the sodium fusidate in situ into Fusidic acid of the preferred embodiment no. 2 comprises the steps of:
  a. heating purified water in the range from 20% (w/w) to 75% (w/w), preferably 30% (w/w) to 50% (w/w), more preferably 35% (w/w) to 45% (w/w) in a water-phase vessel to 70° C. to 80° C.,
  b. adding to said water-phase vessel a preservative, selected from a group comprising Methylparaben, Propylparaben, Chlorocresol, Potassium sorbate, Benzoic acid and the like, either singly or any combination thereof, in an amount between 0.05% (w/w) to 0.5% (w/w), preferably 0.3% (w/w), more preferably 0.2% (w/w), more preferably Benzoic acid,
  c. mixing the mixture using an agitator at 10 to 50 RPM while maintaining the temperature of the mixture at 70° C. to 80° C.,
  d. adding waxy materials, selected from a group comprising White soft paraffin, Liquid Paraffin, Hard paraffin and the like, either singly or any combination thereof, in an amount between 5% (w/w) to 20% (w/w), preferably 15% (w/w), more preferably 12.5% (w/w), to an oil-phase vessel and melting said wax by heating to 70° C. to 80° C.,
  e. adding to said oil-phase vessel a primary emulsifier, preferably in the form of a non ionic Surfactant, selected from a group comprising Cetostearyl alcohol, Cetomacrogol-1000, either singly or any combination thereof, preferably Cetostearyl alcohol in an amount between 1% (w/w) to 15% (w/w), preferably 15% (w/w), more preferably 12.5% (w/w), and optionally a secondary emulsifier selected from a group comprising Polysorbate-80, Span-80 and the like, preferably Polysorbate-80, in an amount between 1 to 5% w/w, more preferably 2% w/w and mixing the mixture thoroughly, preferably using an agitator, at 10 to 50 RPM while maintaining the temperature of the mixture at 70° C. to 80° C.,
  f. transferring under vacuum in the range of minus 1000 to minus 300 mm of mercury and at 70° C. to 80° C. the contents of the water-phase and oil-phase vessels to a mixing vessel and mixing the mixture thoroughly, preferably using an agitator, at 10 to 50 RPM to form an emulsion,
  g. cooling said emulsion to 45° C. preferably by circulating cold water, preferably at 8° C. to 15° C. from a cooling tower in the jacket of the mixing vessel,
  h in an API-vessel adding a co-solvent, selected from a group comprising Propylene Glycol, Hexylene Glycol, PolyEthylene Glycol-400 and the like, either singly or any combination thereof, in an amount between 5% (w/w) to 40% (w/w), preferably 30% (w/w), more preferably 25% (w/w), preferably propylene glycol, subjecting the contents of said API-vessel to inert gas flushing, said inert gas being preferably nitrogen, and adding sodium fusidate to the mixture, said sodium fusidate added in an amount between 0.1% (w/w) to about 25% (w/w), preferably from about 0.5% (w/w) to about 5% (w/w) and more preferably about 2.08% (w/w), and dissolving said Sodium Fusidate in the mixture, i adjusting the pH of the mixture in the API-vessel of step h to below 2 by using an acid, selected from a group comprising acids such as HCl, H2So4, HNO3, Lactic acid and the like, either singly or any combination thereof, preferably Nitric acid in an amount between about 0.005% (w/w) to 0.5% (w/w), preferably 0.3% (w/w), more preferably 0.25% (w/w), j transferring the contents of the API-vessel of step i to the mixing vessel of step g with continuous stirring at 10 to 50 RPM and homogenizing the mixture at 1000 to 3000 RPM under inert gas flushing and under vacuum of minus 1000 to minus 300 mm of mercury, said inert gas being preferably nitrogen, k in a separate vessel adding an acid, selected from a group comprising acids such as HCl, H2So4, HNO3, Lactic acid and the like, either singly or any combination thereof, preferably Lactic acid in an amount between about 0.005% (w/w) to 0.5% (w/w), preferably 0.3% (w/w), more preferably 0.1% (w/w), and purified water from about 0.1% (w/w) to 10% (w/w), preferably 8% (w/w), more preferably 5% (w/w) to form a mixture and dissolving the said biopolymer, Chitosan in an amount between about 0.01% and about 1% by weight, preferably from about 0.01% w/w to about 0.5% w/w and most preferably about 0.25% w/w, l transferring the contents of the biopolymer mixture of step k to the mixing vessel of step g with continuous stirring at 10 to 50 RPM and homogenizing the mixture at 1000 to 3000 RPM under inert gas flushing and under vacuum of minus 1000 to minus 300 mm of mercury, said inert gas being preferably nitrogen, m cooling the contents of the mixing vessel to 30° C. to 37° C. using circulation of cooled water from a cooling tower at 8° C. to 15° C. into the jacket of mixing vessel, n turning off the agitator and the homogenizer and removing the mixture of the Mixing vessel of step m to a storage container.

Embodiment No. 8: In an embodiment of the present invention, the co-solvent of step h of the embodiment no. 7 above also serves as a humectant. However, in another embodiment of the invention, an additional humectant may be added, selected from a group comprising Glycerin, Sorbitol, Propylene glycol and the like, either singly or any combination thereof, to form a from about 5% (w/w) to 40% (w/w), preferably 30% (w/w), more preferably 25% (w/w).

Embodiment No. 9: In another embodiment of the present invention the process described in embodiment no. 8 further incorporates adding a chelating agent, selected from a group comprising Disodium EDTA and the like, either singly or any combination thereof, to form a from about 0.01% (w/w) to 1% (w/w), preferably 0.5% (w/w), more preferably 0.1% (w/w).

Embodiment No. 10: In yet another embodiment of the present invention the process described in embodiments no. 8 and 9 further incorporate a buffering agent selected from a group comprising Di Sodium Hydrogen Ortho Phosphate, Sodium Hydrogen Ortho Phosphate and the like from about 0.001% (w/w) to 1.00% (w/w), preferably 0.05% (w/w), more preferably 0.5% (w/w).

Embodiment No. 11: In a further embodiment of the present invention the process described in embodiments no. 8 to 10 further incorporate an anti oxidants selected from a group comprising Butylated Hydroxy Anisole, Butylated Hydroxy Toluene and the like from about 0.001% (w/w) to 5% (w/w), preferably 0.1% (w/w), more preferably 0.01% (w/w).

Embodiment No. 12: Yet another process of making the composition as per the preferred embodiments is disclosed, said process comprises the steps of:

a. heating purified water in the range from 20% (w/w) to 75% (w/w), preferably 30% (w/w) to 50% (w/w), more preferably 35% (w/w) to 45% (w/w) in a water-phase vessel to 70° C. to 80° C., b. adding to said water-phase vessel a preservative, selected from a group comprising Methylparaben, Propylparaben, Chlorocresol, Potassium sorbate, Benzoic acid and the like, either singly or any combination thereof, in an amount between 0.05% (w/w) to 0.5% (w/w), preferably 0.3% (w/w), more preferably 0.2% (w/w), more preferably Benzoic acid, c. adding to said water-phase vessel of step b, a chelating agent, selected from a group comprising Disodium EDTA and the like, either singly or any combination thereof, in an amount between 0.01% (w/w) to 1% (w/w), preferably 0.5% (w/w), more preferably 0.1% (w/w), d. adding to said water-phase vessel of step c, a buffering agent selected from a group comprising Di Sodium Hydrogen Ortho Phosphate, Sodium Hydrogen Ortho Phosphate and the like in an amount between 0.001% (w/w) to 1.00% (w/w), preferably 0.05% (w/w), more preferably 0.5% (w/w).

e. mixing the mixture of step d using an agitator at 10 to 50 RPM while maintaining the temperature of the mixture at 70° C. to 80° C., f. adding waxy materials, selected from a group comprising White soft paraffin, Liquid Paraffin, Hard paraffin and the like, either singly or any combination thereof, in an amount between 5% (w/w) to 20% (w/w), preferably 15% (w/w), more preferably 12.5% (w/w), to an oil-phase vessel and melting said wax by heating to 70° C. to 80° C., g. adding to said oil-phase vessel of step f, a primary emulsifier, preferably in the form of a non ionic Surfactant, selected from a group comprising Cetostearyl alcohol, Cetomacrogol-1000, either singly or any combination thereof, preferably Cetostearyl alcohol in an amount between 1% (w/w) to 15% (w/w), preferably 15% (w/w), more preferably 12.5% (w/w), and optionally a secondary emulsifier selected from a group comprising Polysorbate-80, Span-80 and the like, preferably Polysorbate-80, preferably in an amount between 1% (w/w) to 5% w/w, more preferably 2% w/w and mixing the mixture thoroughly, preferably using an agitator, at 10 to 50 RPM while maintaining the temperature of the mixture at 75° C.+/−5° C., h. transferring under vacuum in the range of minus 1000 to minus 300 mm of mercury and at 75° C.+/−5° C. the contents of the water-phase and oil-phase vessels to a mixing vessel and mixing the mixture thoroughly, preferably using an agitator, at 10 to 50 RPM to form an emulsion, i. cooling said emulsion to 45° C. preferably by circulating cold water, preferably at 8° C. to 15° C. from a cooling tower in the jacket of the mixing vessel, j. in an API-vessel adding a co-solvent, selected from a group comprising Propylene Glycol, Hexylene Glycol, PolyEthylene Glycol-400 and the like, either singly or any combination thereof, in an amount between 5%

(w/w) to 40% (w/w), preferably 30% (w/w), more preferably 25% (w/w), preferably propylene glycol, and dissolving an antioxidant, selected from a group comprising Butylated Hydroxy Anisole, Butylated Hydroxy Toluene and the like, either singly or any combination thereof, in an amount between 0.001% (w/w) to 5% (w/w), preferably 0.1% (w/w), more preferably 0.01% (w/w), preferably Butylated Hydroxy Toluene in said glycol by continuous mixing, k. subjecting the contents of said API-vessel to inert gas flushing, said inert gas being preferably nitrogen, and adding Sodium Fusidate to the mixture said sodium fusidate being added in an amount between 0.1% (w/w) to about 25% (w/w), preferably from about 0.5% (w/w) to about 5% (w/w) and more preferably about 2.08% (w/w), and dissolving said Sodium Fusidate in the mixture, l. adjusting the pH of the mixture in the API-vessel of step k to below 2 by using an acid, selected from a group comprising acids such as HCl, H2So4, HNO3, Lactic acid and the like, either singly or any combination thereof, preferably Nitric acid in an amount between 0.005% (w/w) to 0.5% (w/w), preferably 0.3% (w/w), more preferably 0.25% (w/w), m. transferring the contents of the API-vessel of step 1 to the mixing vessel of step i with continuous stirring at 10 to 50 RPM and homogenizing the mixture at 1000 to 3000 RPM under inert gas flushing and under vacuum of minus 1000 to minus 300 mm of mercury, said inert gas being preferably nitrogen, n. in a separate vessel adding an acid, selected from a group comprising acids such as HCl, H2So4, HNO3, Lactic acid and the like, either singly or any combination thereof, preferably Lactic acid to form a from about 0.005% (w/w) to 0.5% (w/w), preferably 0.3% (w/w), more preferably 0.1% (w/w), and purified water from about 0.1% (w/w) to 10% (w/w), preferably 8% (w/w), more preferably 5% (w/w) to form a mixture and dissolving the said biopolymer, Chitosan in an amount between about 0.01% and about 1% by weight, preferably from about 0.01% w/w to about 0.5% w/w and most preferably about 0.25% w/w, o. transferring the contents of the biopolymer mixture of step n to the mixing vessel of step i with continuous stirring at 10 to 50 RPM and homogenizing the mixture at 1000 to 3000 RPM under inert gas flushing and under vacuum of minus 1000 to minus 300 mm of mercury, said inert gas being preferably nitrogen, p. cooling the contents of the mixing vessel of step o to 30° C. to 37° C. using circulation of cooled water from a cooling tower at 8° C. to 15° C. into the jacket of mixing vessel q. turning off the agitator and the homogenizer and removing the mixture of said mixing vessel of step n to a storage container.

The co-solvent of step j also serves as a humectant. However, in an embodiment of the invention, an additional humectant may be added, selected from a group comprising Glycerin, Sorbitol, Propylene glycol and the like, either singly or any combination thereof, to form a from about 5% (w/w) to 40% (w/w), preferably 30% (w/w), more preferably 25% (w/w).

The cream obtained using the process of the present invention is homogenous and white to off white in colour and viscous in consistency. The pH of the product made using the process of the present invention is from about 3 to 6. On the other hand, Sodium Fusidate ointments that are commercially available are greasy and cosmetically non elegant.

It is essential that the active drug penetrates the skin for the optimum bio-dermal efficacy. The particle size of the active drug plays an important role here. It is necessary that the active drug is available in a finely dispersed form for the product to be being efficacious. Also this is to be achieved in the safe pH compatible environment of skin (4.0 to 6.0). To achieve all these, it is essential to choose proper vehicles or co-solvents for the dissolution or dispersion of the drug.

Particle size analysis was carried out on the cream made using the process of the present invention and on some commercially available product samples (samples A, C, D, F, G, and K). Maximum and minimum particle sizes, mean particle size and standard deviation and the coefficient of variation were assessed.

TABLE 8

Particle size analysis

| | Minimum Particle Size (μm) | Maximum Particle Size (μm) | Mean Particle Size (μm) | Standard Deviation | Coefficient of Variation |
|---|---|---|---|---|---|
| Present Invention | 2.33 | 16.30 | 10.01 | 3.982 | 0.397 |
| A | 7.23 | 39.58 | 18.09 | 9.251 | 0.511 |
| C | 6.07 | 32.69 | 14.11 | 6.692 | 0.474 |
| D | 9.8 | 27.52 | 18.48 | 4.98 | 0.269 |
| F | 7.93 | 19.90 | 14.82 | 4.033 | 0.272 |
| G | 7.29 | 29.48 | 15.25 | 6.065 | 0.398 |
| K | 5.75 | 32.63 | 16.80 | 8.112 | 0.483 |

The particle size distribution analysis results indicated in table 8 clearly indicate the presence of Fusidic acid of fine particle size in the product of the present invention, the size that is advantageously much reduced than the conventional products. This is attributed to the fact that the instant product is made using Sodium Fusidate using in situ conversion of Sodium Fusidate to Fusidic acid in a finely dispersed form. All of the measured parameters are better than those found for the commercially available creams containing Fusidic acid. This is another clear advantage of the product disclosed herein over the commercially available products.

The product of the present invention is efficacious due to the pronounced antibacterial activity of the regenerated Fusidic acid which is available in reduced particle size than the conventional products, and in a finely dispersed form.

The inventor has screened different co-solvents such as Propylene Glycol, Hexylene Glycol, PolyEthyleneGlycol-400 & the like and dissolved the Sodium Fusidate in one of above co-solvents varying from about 5% (w/w) to 40% (w/w) under inert gas purging and under vacuum and converted to Fusidic acid in-situ by adding an acid such as HCl, $H_2SO_4$, $HNO_3$, Lactic acid and the like from about 0.005% (w/w) to about 0.5% (w/w) under stiffing and obtained Fusidic acid in more stabilized and solution form, which makes our final product in a cream base which easily penetrates the skin and highly efficacious, and also highly derma compatible by having a pH of about 3.0 to about 6.0.

The stability of the product is confirmed by the stability studies performed for 6 months as per ICH guidelines and a comparison of stress studies done for in-house product with those on samples of commercially available comparable products.

Experimental Data:

API-stability experiments were carried out (see tables 10-15) using the product of the present invention and products currently commercially available. Tests were carried out to observe (or measure as appropriate) the physical appearance of the product, the pH value and assay of the API over a period of time. Tests were also carried out to assess the stability by subjecting the product to stress studies such as autoclave test and oxydative degradation test. Further, in vitro antimicrobial zone of inhibition studies and preclinical studies such as blood clotting studies & burns wound healing studies were also carried out over a period of time. Each gram of product of the present invention used for the tests contained Sodium Fusidate as the starting raw material in the amount required to produce approximately 2% (w/w) Fusidic acid in the finished product.

The product used for the Stability Studies, Autoclave and Oxidative degradation tests contained approximately 10% extra API (overages). The product of the present invention used for studies contained Fusidic acid cream prepared using Sodium Fusidate as starting material. It was packaged in an aluminium collapsible tube and each gram of the product contained 20.8 mg of Sodium Fusidate (in conformance with BP), which is equivalent to 20 mg of Fusidic acid (BP conformant). The details of the analysis on commercially available comparable products (Fusidic Acid creams) are provided in the tables 14 and 15 as appropriate.

It is apparent from tables 10-12 that on all counts, the pH value, the physical appearance, and stability, the product of the present invention is quite good. Table 13 provides reference dates for samples A-I which were taken from commercially available creams of Fusidic acid and used for analysis.

The present invention will be further elucidated with reference to the accompanying example containing the composition and stability studies data, which are however not intended to limit the invention in any way whatever The composition of the final cream is given in the table 9 below.

EXAMPLE

TABLE 9

Fusidic acid (equivalent of Sodium Fusidate 2.08% w/w) + Chitosan 0.25% (w/w) Cream

| S. No | Ingredients | Specification | Qtty For 350 Kg | % w/w |
|---|---|---|---|---|
| 1 | Sodium Fusidate (equivalent to make fusidic acid 2%) | BP | 7.28 kg | 2.08 |
| 2 | Chitosan | USP/NF | 0.875 kg | 0.25 |
| 3 | Lactic acid | IP | 0.350 kg | 0.1 |
| 4 | Cetostearyl Alcohol | IP | 43.75 kg | 12.5 |
| 5 | White Soft Paraffin | IP | 43.75 kg | 12.5 |
| 6 | Polysorbate 80 | IP | 7.0 kg | 2 |
| 7 | Propylene Glycol | IP | 87.5 kg | 25 |
| 8 | Benzoic Acid | IP | 0.7 kg | 0.2 |
| 9 | Butylated Hydroxy Toluene | IP | 0.035 kg | 0.01 |
| 10 | Disodium Edetate | IP | 0.35 kg | 0.1 |
| 11 | 1M Nitric Acid solution | IP | 14.0 l | 4 |
| 12 | Disodium hydrogen ortho phosphate | IP | 1.75 kg | 0.5 |
| 13 | Purified Water | IP | 142.7 | 40.77 |

PRODUCT: SODIUM FUSIDATE CREAM
PACK: Aluminum Collapsible Tube
Composition: For each g: Sodium Fusidate BP Equivalent to Fusidic Acid BP 2%

TABLE 10

Description Test, Batch No. SCC-41

| Conditions | Initial | 1 Month | 2 Months | 3 Months | 6 Months |
|---|---|---|---|---|---|
| 40° C. 75% RH | Homogenous White to off White viscous cream | same as initial | same as initial | same as initial | same as initial |

TABLE 10-continued

Description Test, Batch No. SCC-41

| Conditions | Initial | 1 Month | 2 Months | 3 Months | 6 Months |
|---|---|---|---|---|---|
| 30° C. 65% RH | | same as initial | same as initial | same as initial | same as initial |
| 25° C. 60% RH | | same as initial | same as initial | same as initial | same as initial |
| Temp cycling | | same as initial | — | — | — |
| Freezthaw | | same as initial | — | — | — |

Measured parameter: Physical appearance
Best value of measured parameter: Homogeneous White to off White Viscous cream;
Method of measurement: Observation by naked eye

TABLE 11 pH Test, Batch No. SCC-41

| Conditions | Initial | $1^{st}$ Month | $2^{nd}$ Month | $3^{rd}$ Month | $6^{th}$ Month |
|---|---|---|---|---|---|
| 40° C. 75% RH | 4.32 | 4.31 | 4.31 | 4.30 | 4.29 |
| 30° C. 65% RH | — | 4.32 | 4.31 | 4.30 | 4.30 |
| 25° C. 60% RH | — | 4.32 | 4.32 | 4.31 | 4.30 |
| Temperature cycling | — | 4.28 | — | — | — |
| Freezthaw | — | 4.29 | — | — | — |

Measured parameter: pH;
Limits of measured parameter: 3-6
Method of measurement: Digital pH Meter

TABLE 12

Assay (%) Test, Batch No. SCC-41

| Conditions | Initial | $1^{st}$ Month | $2^{nd}$ Month | $3^{rd}$ Month | $6^{th}$ Month |
|---|---|---|---|---|---|
| 40° C. 75% RH | 109.10 | 108.86 | 108.66 | 108.21 | 108.05 |
| 30° C. 65% RH | — | 108.73 | 108.71 | 108.58 | 108.31 |
| 25° C. 60% RH | — | 108.89 | 108.75 | 108.64 | 108.45 |
| Temperature cycling | — | 108.13 | — | — | — |
| Freezthaw | — | 108.22 | — | — | — |

Measured parameter: Assay (%);
Limits of measured parameter: 90-110
Method of measurement: HPLC Method

TABLE 13

| Sample Number | Mfg. Date | Expiry Date |
|---|---|---|
| Present invention | October 2009 | September 2011 |
| Sample A | August 2009 | July 2011 |
| Sample B | August 2009 | July 2011 |
| Sample C | July 2009 | June 2011 |
| Sample D | July 2009 | June 2011 |
| Sample E | August 2009 | July 2011 |
| Sample F | August 2009 | July 2011 |
| Sample G | August 2009 | July 2011 |
| Sample H | July 2009 | June 2011 |
| Sample I | December 2009 | November 2011 |

TABLE 14

Autoclave Analysis (%) Test,
Measured parameter: Assay (%)
Limits of measured parameter: 90-110%
Method of measurement: HPLC Method

| Sr. No | Name of the Products and Details | Analysis-I (%) Initial | Analysis-I (%) After Autoclave | Analysis-I (%) Drop in % | Analysis-II (%) Initial | Analysis-II (%) After Autoclave | Analysis-II (%) Drop in % | Average drop of Analysis-I & Analysis-II (%) |
|---|---|---|---|---|---|---|---|---|
| 1 | Present invention | 110.47 | 104.61 | 5.86 | 110.62 | 104.86 | 5.76 | 5.81 |
| 2 | Sample A | 101.81 | 91.79 | 10.02 | 100.93 | 91.65 | 9.28 | 9.65 |
| 3 | Sample B | 92.69 | 83.54 | 9.15 | 91.13 | 83.08 | 8.05 | 8.6 |
| 4 | Sample C | 110.47 | 98.56 | 11.91 | 110.2 | 99.21 | 10.99 | 11.45 |
| 5 | Sample D | 101.3 | 94.84 | 6.46 | 102.13 | 94.65 | 7.48 | 6.97 |
| 6 | Sample E | 100.99 | 94.51 | 6.48 | 100.21 | 93.51 | 6.70 | 6.59 |
| 7 | Sample F | 96.33 | 84.15 | 12.18 | 95.88 | 85.12 | 10.76 | 11.47 |
| 8 | Sample G | 104.75 | 93.19 | 11.56 | 103.25 | 93.12 | 10.13 | 10.84 |
| 9 | Sample H | 101.26 | 88.35 | 12.91 | 100.86 | 87.98 | 12.88 | 12.89 |
| 10 | Sample I | 101.58 | 87.06 | 14.52 | 100.61 | 88.01 | 12.6 | 13.56 |

TABLE 15

Oxidative degradation Analysis (%) Test,

| Sr. No | Name of the Products and Details | Analysis(%) Initial | Analysis(%) After Oxidation | Degradation in % |
|---|---|---|---|---|
| 1 | Present invention | 110.47 | 106.75 | 3.72 |
| 2 | Sample A | 101.81 | 95.63 | 6.18 |
| 3 | Sample B | 92.69 | 83.15 | 9.54 |
| 4 | Sample C | 110.47 | 101.93 | 8.54 |
| 5 | Sample D | 101.3 | 93.25 | 8.05 |
| 6 | Sample E | 100.99 | 95.47 | 5.52 |
| 7 | Sample F | 96.33 | 90.70 | 5.63 |
| 8 | Sample G | 104.75 | 96.46 | 8.29 |
| 9 | Sample H | 101.26 | 94.53 | 6.73 |
| 10 | Sample I | 101.58 | 88.92 | 12.66 |

Measured parameter: Assay (%)
Limits of measured parameter: NA
Method of measurement: HPLC Method Inference from Table 14: The assay results of Autoclave analysis (121° C. applied for 15 Minutes) indicate that the commercially available samples of Fusidic acid cream (Sr. Nos. 2-10) show more percentage drop in API content than for the product of the present invention (Sr. no. 1).

Inference from Table 15: The above Assay results of Oxidative degradation analysis (30% Hydrogen peroxide Solution over a period of 12 hours) indicate that the various Market samples of Fusidic acid cream (Sr. Nos. 2-10) show significantly higher API degradation (indicated by the percentage drop in API content) than for the product of the present invention (Sr. no. 1).

From the above data, it is evident that product of the present invention is quite stable at ambient conditions and also at elevated temperature & humid conditions of storage. Also the autoclave studies & Oxidative degradation studies further confirm the stability of the product. This is a major advantage over the currently available Fusidic acid creams. The stability of the product is further ascertained by the shelf-life prediction of the formulation using arrhenius plot of degradation employing Nova-LIMS software.

The antimicrobial/antibacterial activity of the product is confirmed by the in vitro Antimicrobial Zone of Inhibition studies for the product against Staphylococcusaureus. The details of the studies are detailed below in Table 16.

TABLE 16

| S. No | Sample | Dose | Zone Diameter Range (mm) | Inference |
|---|---|---|---|---|
| 1 | Reference standard (Fusidic acid) | 10 mcg | 21-33 | Sensitive |
| | | 20 mcg | 20-30 | Sensitive |
| | | 50 mcg | 25-32 | Sensitive |
| 2 | Positive control (Penicillin G) | 10 Units | 21-27 | Resistant |
| 3 | Negative control (DMSO 1%) | NA | NIL | NIL |
| 4 | Sample (Test Substance) - product of the present invention 2%) | 10 mcg | 21-23 | Sensitive |
| | | 20 mcg | 24-26 | Sensitive |
| | | 50 mcg | 21-24 | Sensitive |

From the above data it is evident that the product has adequate antimicrobial/antibacterial activity to treat primary and secondary bacterial infections.

A comparison of table 9 with tables 3 to 7 will illustrate the difference in the products that would be based on the conventional drug design and the innovative approach adopted in the present invention.

Method of Application of the Cream:

The cream is applied after thorough cleansing and drying the affected area. Sufficient cream should be applied to cover the affected skin and surrounding area. The cream should be applied two—four times a day depending upon the skin conditions for the full treatment period, even though symptoms may have improved.

Experiments:

Experiments were carried out with the cream in laboratory as well as using suitable animal models inflicted with excision wounds. Four aspects were tested—wound contraction, epithelisation, blood clotting time, and film forming. These aspects together would suggest that the microbes were immobilized thereby leading to effective wound healing.

A. Wound Contraction:

Excision wound healing activity of the cream of the present invention was determined through animal testing. An excision wound 2.5 cm in diameter was inflicted by cutting away full thickness of the skin. The amount of contraction of the wound observed over a period indicated that the cream of present invention provides significantly improved wound contraction than that achieved through application of a conventional cream.

B. Period Of Epithelisation:

Epithelisation of the wound occurred within shorter number of days using the cream of the present invention as compared to the days taken for epithelisation using the conventional cream Therefore one benefit of the cream of the present invention is that it facilitates faster epithelisation of the skin than through the use of conventional creams.

C. Blood Clotting:

Blood clotting time was observed in both groups of animals, untreated control group and the test group of animals treated with the product of the present invention. Statistically significant decrease in the blood clotting time in treated group animals was observed when compared with that of the control group animals. The mean percent reduction of 35-45% was observed for the blood clotting time using the product of the present invention.

Film Forming Properties:

It is evident from FIG. 1 that chitosan does not lose its film forming property in the presence of the excipients used for cream preparations in the present invention.

Results And Discussion:

It is evident that the properties of chitosan when used in formulations containing the excipients used in the current invention are not compromised in any way. This has been achieved through a careful selection of excipients. For example, our experiments show that widely used excipients such as xanthan gum or carbomer precipitate in combination with chitosan due to cationic, anionic interactions.

The therapeutic impact, as observed from the animal testing, of the addition of chitosan to Sodium Fusidate antibacterial agent, is shown in the following table by considering various aspects of therapeutic cure of a compromised skin condition:

TABLE 17

Figure 2:
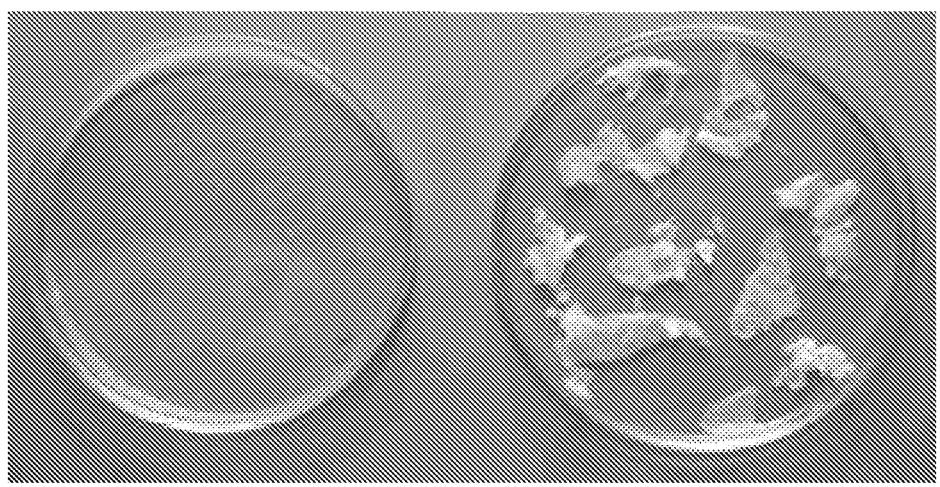

| Therapeutic aspect | Existing creams | Products of the present invention |
|---|---|---|
| 1. Blood Clotting time | None explicitly claimed | Statistically significant reduction in clotting time as evidenced by pre-clinical animal trials |
| 2. Immobilisation of microbes | None explicitly claimed | Expected to immobilise the surface microbes because of the cationic charge of chitosan |
| 3. Epidermal growth support | None explicitly claimed | It is well known that chitosan possesses properties that have significant complimentary action on epidermal growth. This functional aspect of chitosan is preserved in the product of the present invention |
| 4. Micro-film forming | None explicitly claimed | Yes (see FIG. 2) |
| 5. Overall wound healing medicinal effect | Standard as per existing products | Provides superior healing properties |

TABLE 18

Wound healing properties of the present invention

| Measurement criterion | Groups | Mean +/− SE (days) | P value | Statistical Significance |
|---|---|---|---|---|
| Period of epithelisation | Control | 21.75 +/− 0.25 | — | |
| | Present invention | 17.25 +/− 1.5 | 0.042 | Significant |
| % of wound contraction (mean +/− SEM) on day 4 after wound infliction | Control | 0.028 +/− 3.76 | — | |
| | Present invention | 34.03 +/− 5.66 | 0.004 | Significant |
| % of wound contraction (mean +/− SEM) on day 8 after wound infliction | Control | 15.63 +/− 4.24 | | |
| | Present invention | 53.4 +/− 3.9 | 0.0001 | Significant |
| % of wound contraction (mean +/− SEM) on day 12 after wound infliction | Control | 23.4 +/− 3.44 | | |
| | Present invention | 71.6 +/− 7.67 | 0.0001 | Significant |
| % of wound contraction (mean +/− SEM) on day 16 after wound infliction | Control | 58.1 +/− 8.4 | | |
| | Present invention | 92.4 +/− 7.5 | 0.0001 | Significant |

Wound healing studies were carried out on animals and using the cream of the present invention. The results are incorporated in table 18.

It is evident that the film forming ability of the chitosan incorporated in the cream allows better access of the antibacterial agent, Sodium Fusidate to the infected area and results in better functioning of these API.

The therapeutic efficacy of topically applied cream of the present invention is due to the pronounced antibacterial activity of the Sodium Fusidate against the organisms responsible for skin infections, the unique ability of actives to penetrate intact skin and wound healing & soothing properties of chitosan.

It is further evident from table 18 that the ability of the cream of the present invention to achieve statistically significant level of epithelisation as well as wound contraction is surprisingly greater than the currently available therapies.

It is evident from the foregoing discussion that the present invention offers the following advantages and unique aspects over the currently available dermaceutical compositions for bacterial infections and for wound healing of the skin:

1. The cream of the present invention incorporates a skin-friendly biopolymer in the form of chitosan provides enhanced therapeutic outcomes. This is evident from the reduced blood clotting time, increased epithelial effect, and faster relief from infection and inflammation and wound contraction.
2. The cream of the present invention incorporates a biopolymer without compromising the stability of the cream matrix and without adversely affecting the functioning of known active pharmaceutical ingredients. This has been achieved through a careful selection of functional excipients to bypass undesirable aspects of physio-chemical compatibility/stability and bio-release.
3. The cream of the present invention provides an integrated uni-dose or a single-dose therapy hitherto unavailable in prescription dermaceutical formulations.

4. The novel cream of the present invention is adequately stable/efficacious at ambient conditions and does not need special temperature control during transportation/storage—hence will go a long way in achieving these social objectives.

According to another embodiment of the present invention, there is also provided a process for treating bacterial skin infections, and wound healing involving contacting human skin with the above-disclosed composition.

While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

The invention claimed is:

1. A medicinal cream comprising: (a) fusidic acid which is made in situ under an oxygen-free environment using sodium fusidate, wherein the cream comprises fusidic acid made by dissolving sodium fusidate in a co-solvent under inert gas purging and under vacuum, and converting the sodium fusidate to fusidic acid in situ by adding an acid under stirring; (b) a biopolymer; and (c) a cream base comprising at least one of each of a primary and secondary emulsifier, a waxy material, and water.

2. The medicinal cream of claim 1, wherein the biopolymer comprises chitosan.

3. The medicinal cream of claim 2, further comprising a preservative.

4. The medicinal cream of claim 3, wherein:
the fusidic acid is present in an amount from about 0.1% (w/w) to about 25% (w/w);
the chitosan is present in amount between about 0.01% (w/w) and about 1% (w/w);
the emulsifier is selected from a group consisting of cetostearyl alcohol, cetomacrogol-1000, polysorbate-80, and span-80, and combinations thereof, in an amount from about 1% (w/w) to 20% (w/w);
the waxy material is selected from a group consisting of white soft paraffin, liquid paraffin, hard paraffin, and combinations thereof, in an amount from about 5% (w/w) to 30% (w/w);
the co-solvent is selected from a group consisting of propylene glycol, hexylene glycol, polyethylene glycol-400, isopropyl myristate, and combinations thereof, in an amount from about 5% (w/w) to 50% (w/w);
the acid is selected from a group consisting of HCl, $H_2SO_4$, $HNO_3$, Lactic acid, and combinations thereof, in an amount from about 0.005% (w/w) to 0.5% (w/w);
the preservative is selected from a group consisting of methylparaben, propylparaben, chlorocresol, potassium sorbate, benzoic acid, and combinations thereof, in an amount from about 0.05% (w/w) to 0.5% (w/w); and
the water is present in an amount in the range of 20% (w/w) to 75% (w/w).

5. The medicinal cream of claim 4, wherein:
the fusidic acid is present in an amount from about 0.5% (w/w) to about 5% (w/w); and
the chitosan is present in amount between about 0.01% (w/w) and about 0.5% (w/w).

6. The medicinal cream of claim 5, further comprising a buffering agent which is selected from a group consisting of disodium hydrogen orthophosphate, sodium hydrogen orthophosphate, and combinations thereof, in an amount from about 0.001% (w/w) to 1.00% (w/w).

7. The medicinal cream of claim 6, further comprising an antioxidant which is selected from a group consisting of butylated hydroxy anisole, butylated hydroxy toluene and combinations thereof, in an amount from about 0.001% (w/w) to 1% (w/w).

8. The medicinal cream of claim 7 further comprising disodium EDTA in an amount from about 0.05% (w/w) to 1% (w/w).

9. The medicinal cream of claim 8, further comprising a humectant which is selected from a group consisting of glycerin, sorbitol, propylene glycol, and combinations thereof, in an amount from about 5% (w/w) to 50% (w/w).

10. A process to make the medicinal cream of claim 1, the process comprising the step of converting the sodium fiisidate in situ into fusidic acid under an oxygen-free environment and adding the fusidic acid and biopolymer to a cream base.

11. The process of claim 10, comprising the steps of:
a. heating purified water in a water-phase vessel to 70° C. to 80° C.,
b. adding, to the water-phase vessel a preservative, selected from a group consisting of methylparaben, propylparaben, chlorocresol, potassium sorbate, benzoic acid, and combinations thereof to form a mixture,
c. mixing the mixture using an agitator at 10 to 50 RPM while maintaining the temperature of the mixture at 70° C. to 80° C.,
d. adding a waxy material selected from a group consisting of white soft paraffin, liquid paraffin, hard paraffin, and. combinations thereof to an oil-phase vessel and melting the waxy material by heating the waxy material to a temperature between 70° C. to 80° C.,
e. adding, to the oil-phase vessel a primary emulsifier selected from a group consisting of cetostearyl alcohol, cetomacrogol-1000, and combinations thereof, and adding to the oil-phase vessel a secondary emulsifier selected from a group comprising polysorbate-80, span-80, and combinations thereof to form a mixture, and mixing the mixture thoroughly at 10 to 50 RPM While maintaining the temperature of the mixture at 70° C. to 80° C.,
f. transferring under vacuum in the range of minus 1000 to minus 300 mm of mercury and at 70° C. to 80° C. the contents of the water-phase vessel and the contents of the oil-phase vessel to a mixing vessel to form a. mixture and mixing the mixture thoroughly at 10 to 50 RPM to form an emulsion,
g. cooling the emulsion to 45° C.,
h. adding to an API-vessel a co-solvent selected from a group consisting of propylene glycol, hexylene glycol, polyethylene glycol-400, and any combinations thereof, subjecting the contents of the API-vessel to inert gas flushing, adding sodium fusidate to the contents of the API-vessel, and dissolving the sodium fusidate in the contents of the API-vessel to form a mixture,
i. adjusting the pH of the mixture in the API-vessel of step h to below 2 by adding an acid selected from a group consisting of HCl, $H_2SO_4$, $HNO_3$, Lactic acid, and combinations thereof,
j. transferring the contents of the API-vessel of step i to the mixing vessel of step g with continuous stirring at 10 to 50 RPM and homogenizing the mixture at 1000 to 3000 RPM under inert gas flushing and under vacuum of minus 1000 to minus 300 mm of mercury,
k. adding to a separate vessel purified water and an acid selected from a group consisting of HCl, $H_2SO_4$, $HNO_3$, Lactic acid, and combinations thereof, to form a solution and dissolving chitosan in the solution to form a biopolymer mixture, l. transferring the contents of the biopolymer mixture of step k to the mixing vessel of step g with continuous stirring at 10 to 50 RPM and homogenizing the mixture at 1000 to 3000 RPM under inert gas flushing and under vacuum of minus 1000 to minus 300 mm of mercury, m. cooling the contents of the mixing vessel of step j to a temperature of 30° C. to 37° C., n. removing the contents of the mixing vessel of step m to a storage container.

12. The process of claim 11, further comprising adding a humectant to the water-phase vessel of step a, the humectant selected from a group consisting of glycerin, sorbitol, propylene glycol, and any combination thereof.

13. The process of claim 12, further comprising adding disodium EDTA to the water-phase vessel of step a.

14. The process of claim 13, further comprising adding a buffering agent to the water-phase vessel of step a, the buffering agent selected from a group consisting of disodium hydrogen orthophosphate, sodium hydrogen orthophosphate and combinations thereof.

15. The process of claim 14, further comprising adding an antioxidant to the API-vessel of step h, the antioxidant selected from a group consisting of butylated hydroxy anisole, gutylated hydroxyl toluene, and combinations thereof.

16. The process of claim 10, comprising the steps of:

a. heating purified water in a water-phase vessel to 70° C. to 80° C., b. adding to the water-phase vessel a preservative, selected from a group consisting of methylparaben, propylparaben, chlorocresol, potassium sorbate, benzoic acid, and combination thereof, c. adding to the water-phase vessel of step b, a chelating agent comprising disodium EDTA, d. adding to the water-phase vessel of step c, a buffering agent selected from a group consisting of disodium hydrogen orthophosphate, sSodium hydrogen orthophosphate, and combinations thereof, to form a mixture, e. mixing the mixture of step d at 10 to 50 RPM while maintaining the temperature of the mixture at 70° C. to 80° C., f. adding a waxy material selected from a group consisting of white soft paraffin, liquid paraffin, hard paraffin, and combinations thereof, to an oil-phase vessel and melting the waxy material by heating the waxy material to a temperature between 70° C. to 80° C., g. adding, to the oil-phase vessel of step f, a primary emulsifier selected from a group consisting of cetostearyl alcohol, cetomacrogol- 1000, and combinations thereof, and adding to the oil-phase vessel of step f a secondary emulsifier selected from a group consisting of Polysorbate-80, Span-80, and combinations thereof to form a mixture, and mixing the mixture thoroughly at 10 to 50 RPM while maintaining the temperature of the mixture at 75° C. +/−5° C.

h. transferring under vacuum in the range of minus 1000 to minus 300mm of mercury and at 70° C. to 80° C. the contents of the water-phase vessel and the contents of the oil-phase vessel to a mixing vessel, to form a mixture, and mixing the mixture thoroughly at 10 to 50 RPM to form an emulsion, i. cooling the emulsion to 45° C., j. adding to an API-vessel a co-solvent selected from a group consisting of propylene glycol, hexylene glycol, polyEthylene glycol-400, and combinations thereof, and dissolving an antioxidant selected from a group consisting of butylated hydroxy anisole, hutylated hydroxy toluene, and combinations thereof, in the co-solvent by continuous mixing, k. subjecting the contents of the API-vessel to inert gas flushing, adding sodium fusidate to the API-vessel, and dissolving the sodium fusidate in the contents of the API-vessel, l. adjusting the pH of the contents of the API-vessel of step k to below 2 by adding an acid selected from a group consisting of HCl, $H_2SO_4$, $HNO_3$, Lactic acid, and combinations thereof, m. transferring the contents of the API-vessel of step 1 to the mixing vessel of step i with continuous stirring at 10 to 50 RPM and homogenizing the mixture at 1000 to 3000 RPM under inert gas flushing and under vacuum of minus 1000 to minus 300 mm of mercury, n. adding to a separate vessel purified water and an acid selected from a group consisting of HCl, $H_2SO_4$, $HNO_3$, Lactic acid, and combinations thereof, to form a solution and dissolving the chitosan in the solution to form a biopolymer mixture, o. transferring the contents of the biopolymer mixture of step n to the mixing vessel of step i with continuous stirring at 10 to 50 RPM and homogenizing the mixture at 1000 to 3000 RPM under inert gas flushing and under vacuum of minus 1000 to minus 300 mm of mercury, p. cooling the contents of the mixing vessel of step i to 30° C. to 37° C., q. removing the contents of the mixing vessel of step i to a storage container.

* * * * *